(12) United States Patent
Grossmann

(10) Patent No.: US 6,342,585 B1
(45) Date of Patent: Jan. 29, 2002

(54) METHOD OF ACTIVATING DENATURED PROTEIN

(75) Inventor: Adelbert Grossmann, Eglfing (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/202,206

(22) PCT Filed: Jun. 11, 1997

(86) PCT No.: PCT/EP97/03026

§ 371 Date: Feb. 1, 1999

§ 102(e) Date: Feb. 1, 1999

(87) PCT Pub. No.: WO97/47735

PCT Pub. Date: Dec. 18, 1997

(30) Foreign Application Priority Data

Jun. 11, 1996 (DE) .......................................... 961 09 288
Jun. 22, 1996 (DE) .......................................... 961 10 109

(51) Int. Cl.⁷ .......................... C07K 1/00; C07K 14/00; C12P 21/06; C12N 1/14; C12N 1/18
(52) U.S. Cl. ........................ 530/351; 530/350; 530/402; 530/404; 530/408; 530/412; 530/399; 435/69.1; 435/69.4; 435/69.5; 435/254.1; 435/254.2

(58) Field of Search ................................ 435/69.1, 69.4, 435/69.5, 69.52, 69.7, 71.1, 71.2, 113, 243, 254.1, 254.2, 255.1; 530/350, 351, 399, 402, 404, 408, 412

(56) References Cited

U.S. PATENT DOCUMENTS

| 4,766,205 A | * | 8/1988 | Ghosh-Dastidar | ............ 530/402 |
| 4,923,767 A | * | 5/1990 | Bobbitt et al. | ............... 530/351 |
| 5,235,043 A | * | 8/1993 | Collins et al. | ............... 530/399 |

FOREIGN PATENT DOCUMENTS

| AU | B11412 | 2/1988 | ............. C07K/3/08 |
| AU | B17124 | 4/1988 | ............. C07K/3/08 |
| AU | B43385 | 9/1989 | ............. C12N/15/58 |
| AU | B67018 | 11/1990 | ............. C07K/3/08 |
| WO | WO8901046 | 2/1989 | ............. C12P/21/02 |

* cited by examiner

Primary Examiner—N. M. Minniefield
(74) Attorney, Agent, or Firm—Fulbright & Jaworski, LLP

(57) ABSTRACT

The invention relates to a method for forming a mixed disulfide of recombinant proteins, by solubilizing with a denaturing agent in the presence of a disulphide component, and then adding a disulphide component plus a denaturing agent, at a concentration sufficient to form a mixed disulfide.

33 Claims, No Drawings

METHOD OF ACTIVATING DENATURED PROTEIN

The present invention concerns a simplified process for the solubilization and renaturation of denatured proteins, in particular of recombinantly produced denatured proteins.

Sparingly soluble inactive protein aggregates (inclusion bodies) are frequently formed when proteins are produced in prokaryotic cells such as *E. coli*. In order to convert these proteins into their active form it is necessary to solubilize and to renature these proteins. Such processes are known and are for example described in EP-A 0 361 475, EP-A 0 114 506, EP-A 0 093 619, EP-A 0 253 823, WO 87/02673, EP-A 0 364 926 and EP-A 0 241 022. An important factor in the activation which limits the yield of renatured protein is the competing reaction between conversion of the renatured protein into the correctly folded intermediate and an aggregation of several protein molecules. For this reason the concentration of renatured protein in the renaturation solution is an important parameter for the yield of the renaturation process. Aggregation is favoured by increasing concentrations of renatured protein and the relative yield of renatured protein with the conformation of the native protein decreases (critical concentration).

In a large-scale production of recombinant proteins the amount of protein to be renatured is usually much higher than the critical concentration. Since the proteins often have a low solubility in the activation buffer used, this therefore results in considerable disadvantages such as low yield, long time requirement and large buffer volumes.

A process is known from WO 87/02673 in which the inactive soluble protein is solubilized with denaturing agents and reducing agents, subsequently the reducing agent is separated and then heterologous mixed disulfides between protein and for example glutathione are prepared from the solubilized proteins. Such mixed disulfides are advantageous for the further purification and renaturation since after modification of the thiol groups the protein is protected against air oxidation and it is thus stable in a larger pH range. The change in the net charge also facilitates the purification since it enables non-modified proteins to be separated by means of ion exchange chromatography.

In order to form the mixed disulfides, the solubilized, dialysed and reduced protein that has been purified of reducing agents is incubated with a solution which contains a denaturing agent and a disulfide component for the derivatization (e.g. GSSG, cystine, cystamine). A renaturation is carried out in the usual manner after separation of the disulfide component. Although this process is efficient, it requires many individual process steps especially for separation of the reducing agent before the derivatization.

A process for folding and purifying insulin-like growth factor I is known from WO 93/19084. According to this the inclusion bodies are dissolved under reducing conditions, subsequently an excess of oxidizing agent is added without separating the reducing agent. The renaturation is initiated by subsequent dilution (without dialysis) and new addition of reducing agent (to construct a redox system). WO 91/08762 describes the preparation of biologically active platelet derived growth factor. In this process a solubilization is firstly carried out at pH 3 without a reducing agent and subsequently a purification under denaturing conditions. Only afterwards is an oxidizing agent added to produce a derivative. According to EP-A 0 450 386 an extract of inclusion bodies (denatured dissolved NGF protein) is prepared by adding solubilizing buffer with subsequent centrifugation. The extract is then treated with a reducing agent, incubated and oxidized by addition of an oxidizing agent without previous dialysis. Subsequently it is diluted and further components are added for the denaturation. Thus in this process a solubilization is firstly carried out as a separate process step without adding redox active substances. None of these processes is suitable for a pulse renaturation according to U.S. Pat. No. 4,933,434.

In addition processes are known which already allow a derivatization during the solubilization. The method of sulfitolysis has been known for a long time (e.g. Bailey, J. L., Cole, R. D., 1959, J. Biol. Chem. 234, 1733–1739; Cole, R. D., 1967, In: Meth. Enzymol. 11, 206–208; EP 0 114 507). In this process disulfide bridges in proteins are treated with salts of sulfurous acid to form a mixture of 50% thiosulfonated ($RS-SO_3^-$) and 50% free ($RS^-$) protein-SH groups as the reaction product. The latter free SH groups are in turn converted into disulfides by reoxidation (e.g. with copper ions, iodosobenzoate or preferably with tetrathionate) which can be almost completely converted into the thiosulfonate by repeated cycles of the process. This process is relatively simple and can be carried out under mild boundary conditions (e.g. neutral pH value). As already set forth in J. Biol. Chem. 234, 1733 a disadvantage is that the thiosulfonate that is formed is chemically labile, it is not possible to check the completion of the conversion and above all the tryptophan residues are partially destroyed by the reoxidation agent. A further disadvantage is that it is very difficult to completely separate by-products containing thiosulfonated protein-SH groups and oxidizing agents such as the said iodosobenzoate in the final product and it is extremely laborious to detect this analytically. However, this is absolutely necessary for proteins which are intended for a therapeutic application in order to exclude possible side effects of a therapeutic agent that has been chemically modified in such an unphysiological manner.

WO 95/30686 also describes such a sulfitolysis to renature neurotrophic factors of the NGF/BDNF family. A similar process is described for the renaturation of human proinsulin by R. Wetzel et al., Gene 16 (1981) 63–71 as well as by W. F. Heath et al., J. Biol. Chem. 267 (1992) 419–425.

A similar method which avoids the use of reoxidation conditions that damage side chains is also known (Thannhauser, T. W., Konishi, Y., Scheraga, H. A., 1984, Analyt. Biochem. 138, 181–188; Thannhauser, T. W., Scheraga, H. A., 1985, Biochemistry 24, 7681–7688): In this case instead of a reoxidation, the cysteine obtained when the disulfide bridge is reduced is directly derivatized by reaction with 2-nitro-5-(sulfothio)-benzoate; 2-nitro-5-thiobenzoate is released in this process which can be measured photometrically and thus enables a quantification of the converted SH groups. A disadvantage of this method is that a complex chemical substance is introduced whose complete separation from the final product is very time-consuming and difficult to check. Furthermore the authors (Biochemistry 24, 7681) observed that the thiosulfonate obtained is only stable when thiol groups are completely absent. In addition a side chain modification is also observed in this case (deamination of asparagine).

The object of the present invention is to simplify and to improve these processes and to provide stable, storable proteins whose SH groups are derivatized and which can be renatured in a high yield.

Surprisingly it was found that the process according to the invention allows the solubilization and derivatization to be carried out in a single step without having to previously reduce. It is particularly surprising that the derivatization can also take place under acidic conditions (pH value less than 7.0, preferably pH 3–6.5) preferably for neurotrophins such as NGF and that this is achieved without essentially affecting the kinetics and the completeness of a reaction compared to a reaction with thiol components in the usual pH range of about 7–10. It is usually assumed that such reactions can only proceed in the presence of the free thiolate anion; this only occurs in effective concentrations at pH values above about 7 due to the high pK value of thiolate anions of about 9.

The invention therefore concerns a process for producing mixed disulfides composed of a protein and a disulfide component which is characterized in that the protein in an inactive sparingly soluble form (inclusion bodies) is incubated, dissolved and derivatized with a solution of a denaturing agent in a denaturing concentration and in the presence of a disulfide component (molar ratio protein : disulfide component 1:1 to 1:10000, preferably 1:1000) and subsequently the disulfide component is optionally removed. The disulfide component can then be expediently removed by subsequently carrying out a pulse renaturation as described in the U.S. Pat. No. 4,933,434. The derivatized protein according to the invention is stable and can be stored before further processing. This is particularly advantageous since the derivatized protein can be produced by the process according to the invention independently of the renaturation. Hence the derivatized protein is available as an isolated intermediate product for numerous renaturation and purification processes and/or preparations.

Alternatively the incubation to derivatize the protein is carried out in the presence of a reducing agent (e.g. DTT, DTE, GSH, cysteine, cysteamine, salts of sulfurous acid). This can improve the derivatization yield. In this case it is expedient to select the concentration of the reducing agent so that the effectiveness of the disulfide component is not restricted or only to a slight extent; reducing agent concentrations of up to 20 mole percent, preferably up to 10% of the concentration of the disulfide component have turned out to be favourable.

Additional reagents can be preferably added to protect free SH groups which can partially or completely prevent blocking or destruction of these SH groups by heavy metals, radicals or active oxygen species. This class of protecting reagents for example includes EDTA at a concentration of 0.1 to 100 mmol/l or mannitol at a concentration of 1 to 1000 mmol/l.

Disulfide components are understood as substances from the disulfide class e.g. GSSG, cystamine or cystine. Disulfide components are able to derivatize SH groups in proteins after cleavage of a disulfide bridge. The disulfide component is preferably used at a concentration of at least 1 mmol/l or higher, preferably of 1–1000 mmol/l, particularly preferably of 10–200 mmol/l.

It is expedient to use a denaturing agent that is usually used to solubilize denatured protein under oxidizing conditions as the denaturing agent. It is preferable to use guanidinium hydrochloride or other guanidinium salts such as e.g. sulfate, phosphate or thiocyanate as well as urea or derivatives thereof. It is also possible to use mixtures of these denaturing agents.

The concentration of the denaturing agent depends on the type of the denaturing agent and can be easily determined by a person skilled in the art. The concentration of the denaturing agent is adequate if a complete solubilization of the denatured sparingly soluble protein can be achieved. In the case of guanidine hydrochloride these concentrations are usually 3–8 mol/l, preferably 6–8 mol/l. In the case of urea the concentration is usually 6–10 mol/l.

"Protein in an inactive sparingly soluble form" is understood as a protein which is for example formed by recombinant production in prokaryotes. Such proteins are usually formed when eukaryotic proteins are overexpressed in prokaryotes and the protein is not transported in an active form into the periplasm or into the cell supernatant. In this case the recombinantly produced protein remains in the cytoplasm or periplasm in an insoluble and aggregated form. Such aggregates, their isolation and purification are described for example in Marston F. A. O., Biochem. J. 214 (1986) 1–12. The prokaryotic cells are lysed after the fermentation to isolate inclusion bodies.

The cell lysis can be carried out according to the usual methods e.g. by means of ultrasound, high pressure dispersion or lysozyme. It is preferably carried out in a buffer solution that is suitable for adjusting a neutral to weakly acidic pH value as a suspension medium such as e.g. 0.1 mol/l Tris-HCl. After cell lysis the insoluble components (inclusion bodies) are separated in any desired manner, preferably by centrifugation or by filtration after washing with agents which do not interfere with the proteins but dissolve foreign cell proteins as completely as possible e.g. water or phosphate buffer optionally with addition of mild detergents such as Brij®. Subsequently the precipitate (pellet) is subjected to the process according to the invention for solubilization and derivatization.

The process according to the invention is carried out in a neutral to alkaline pH range, preferably between pH 6 and 10, particularly preferably in the pH range between 7 and 8. All common buffers are suitable as buffer solutions; when guanidinium hydrochloride is used as a denaturing agent it is not necessary to add buffers because of its buffering action. Buffers known to a person skilled in the art are preferably used such as e.g Tris or phosphate. Surprisingly the process according to the invention can also be particularly advantageously used for neurotrophins even under acidic conditions (pH 3–6.5).

The process according to the invention is carried out with the addition of a disulfide component. Preferred disulfide components are e.g. GSSG, cystamine and cystine. Since the derivatization reaction is an equilibrium reaction between protein in the thiol form and the disulfide component or between a mixed disulfide composed of protein and disulfide component on the one hand and the free thiol components i.e. remaining protein thiol groups and, on the other hand, thiol components released from the disulfide component by reaction with the protein in the thiol form, the desired derivatization reaction must be forced by a high excess of the disulfide component. The conditions that are necessary for this are very different from protein to protein. It is preferable to use a concentration range of the disulfide component from 10 mmol/l up to the saturation limit (e.g. ca. 200–300 mmol/l in the case of GSSG depending on the pH value of the preparation, ca. 700 mmol/l for cystamine), the concentration range is particularly preferably 50–100% of the saturation concentration of the disulfide component.

It is also preferable to add a reducing agent in the process according to the invention. Reducing agents from the mercaptan group are particularly preferred such as reduced glutathione (GSH) or 2-mercaptoethanol, dithioerythritol (DTE) or dithiothreitol (DTT) at a concentration of 0.01–50 mmol/l, preferably 0.1–10 mmol/l. Reducing agents such as salts of sulfurous acid e.g. sodium sulfite are additionally preferred. Although the addition of one of these reducing agents is not a prerequisite for successfully carrying out the reaction, this addition can, however, lead to an improved yield when the protein is reactivated depending on the treated protein.

The process according to the invention is preferably carried out at room temperature during a period of 0.1–100 hours, preferably 1–24 hours, particularly preferably 2–4 hours. Other conditions such as heating to about 60° C. or a process with cooling to about 0° C. are, however, also suitable. In order to prevent oxidation of the reducing agent by atmospheric oxygen and to protect free SH groups, it is expedient to add EDTA preferably in an amount of 1–100 mmol/l, particularly preferably by ca. 10 mmol/l. In order to suppress radical side reactions which can for example occur in solutions containing thiol especially at relatively high pH values it is also expedient to add radical interceptors (quenchers) such as e.g mannitol at a concentration of 1 to 1000 mmol/l, preferably at a concentration of 20 to 200 mmol/l, particularly preferably at a concentration of 50 mmol/l during the renaturation and/or processing of the proteins.

After solubilization/derivatization it is preferable to dialyse against a solution which contains a denaturing agent in a denaturing concentration in order to remove the disulfide component and optionally added reducing agent. The dialysis solution advantageously contains the denaturing agent at the same concentration as in the denaturation/derivatization solution. It is also preferable to dialyse against other denaturing agents at the same molar concentration, e.g. against ca. 1 mmol/l HCl or dilute acetic acid. Furthermore it has also turned out to be expedient to not completely separate the disulfide component; as already explained the derivatization reaction is an equilibrium reaction between free thiol components and (optionally mixed) disulfide components. If all protein thiol groups have not been completely derivatized, there is a risk after separation of the disulfide component that the remaining free thiol components will have a reducing effect on the mixed disulfides that are present and hence that the derivatization yield will subsequently decrease during storage of the derivatized protein. The degree of derivatization of the treated protein must therefore be as high and stable as possible with regard to the intended aim of the derivatization to protect the protein thiol groups against oxidation and against similar destructive side reactions. This can either be achieved by prematurely terminating the dialysis before the concentration of the disulfide component has fallen below a suitable concentration or by dialysing in the dialysis against a dialysis buffer which contains the disulfide component at the required concentration. The concentration required to maintain the degree of derivatization during storage of the derivatized protein depends on the respective treated protein and in particular on the cysteine content of the treated protein and can be in a concentration range of 0–100 mmol/l. With regard to the further use of the derivatized protein for the reactivation reaction, care must be taken that the introduction of the disulfide component in the reactivation process has no or only a negligible effect on the conditions used in this case for the desired oxidative linkage of intermolecular or intramolecular disulfide bridges. For this reason a residual concentration of disulfide component in the derivatized protein of about 1–10 mmol/l has proven to be favourable.

A further subject matter of the invention is a process for producing a renatured protein from its inactive sparingly soluble form obtainable after recombinant production in prokaryotes which is characterized in that the protein in its inactive sparingly soluble form is incubated, dissolved and derivatized with a solution of a denaturing agent in a denaturing concentration and in the presence of a disulfide component (molar ratio protein disulfide component 1:1 to 1:10000, preferably 1:1000), and the dissolved protein assumes a biologically active conformation by changing the strongly denaturing solution into a weakly or non-denaturing solution in which the disulfide bonds with the disulfide component are broken by addition of a redox system and in this manner are newly formed intramolecularly in the protein in such a way that the protein adopts a conformation in which it has its characteristic biological activity.

Such weak denaturing conditions can for example be achieved by dilution or dialysis preferably in the presence of a reducing agent. Weakly denaturing conditions are, in contrast to strongly denaturing conditions, those conditions under which the protein is able to adopt its active conformation and be stable in this conformation. Under strongly denaturing conditions the protein is unstable in this form and tends to denature i.e. to lose its stable three-dimensional structure and the energetically favourable disulfide bond. Strongly denaturing conditions exist for example in solutions of 4–9 mol/l guanidine hydrochloride. Weakly denaturing conditions exist for example between 0.1 and 2 mol/l guanidine hydrochloride. It is also expedient to add arginine at a concentration between 0.1 and 1 mol/l during the renaturation.

The activity of the protein is understood as a biological activity of the protein. If it is a naturally occurring protein or a derivative of a natural protein, its biological activity can be determined by means of the immunological, cell-biological or catalytic properties of the protein.

The activation (renaturation) is preferably carried out at a GSH concentration of 0.1–20 mmol/l, a GSSG concentration of 0.01–10 mmol/l without a denaturing agent or at a non-denaturing concentration of a denaturing agent and the reactivation is preferably carried out over a period of 1–300 hours. In this case the GSH concentration is preferably 0.5–10 mmol/l and/or the GSSG concentration is preferably 0.1–10 mmol/l.

The process according to the invention is suitable for renaturing numerous denatured proteins and in particular recombinantly produced denatured proteins. Such proteins are for example proteases, growth factors, protein hormones, cytokines, plasminogen activators, factor Xa and in particular neurotrophins. Neurotrophins are proteins which are found especially in nerve cells and support the differentiation and the survival of nerve cells. Neurotrophins (e.g. NGF, brain derived nerve growth factor (BDNF), neurotrophins 3, 4/5, 6) are therefore valuable cell therapeutic agents for the treatment of neurodegenerative diseases such as polyneuropathies, Alzheimer's disease or injuries to the brain and spinal cord. Human nerve growth factor (NGF) is a protein which is composed of two subunits (homodimers). The β unit has been found to have the ability to affect the growth of sensory neurones and sympathetic neurones. Mature NGF is composed of 118 amino acids, contains three disulfide bridges and is not glycosylated. Biologically active NGF is present as a dimer. The DNA and amino acid sequence of NGF is described in EP-B 0 121 338 (U.S. Pat. No. 5,169,762). However, it was not possible to obtain active protein by this process. The production of active recombinant NGF is for example described in EP-A 0 329 175, EP-A 0 370 171, in Biochem. Biophys. Res. Commun. 171 (1990) 116–122, EP-A 0 414 151, Gene 70 (1988) 57–65, EP-A 0 450 386 and Gene 85 (1989), 109–114.

Brain derived neurotrophic factor (BDNF) was described by Leibrock et al., Nature 341 (1989) 149–152. BDNF supports the survival of sensory neurones in the central nervous system and appears to be successful in the treatment of Parkinson's disease. Recombinant BDNF can for example be produced according to WO 91/03568 in CHO cells and according to WO 92/22665 in prokaryotes.

The following examples, publications and the sequence protocol further elucidate the invention, the protective scope of which results from the patent claims. The described processes are to be understood as examples which still describe the subject matter of the invention even after modifications.

EXAMPLE 1

Expression of NGF in *E. coli* a) Expression Plasmid

The NGF gene which codes for the mature part was synthesized (SEQ ID NO:4) on the basis of the sequence published by Ullrich et al. (Nature 303: 821, 1983) and by incorporating some modifications in particular in the 5' part. The method of Beattie and Fowle (1991, Nature 352: 548–549) was used for this. In order to facilitate the cloning, a cleavage site for the restriction enzyme EcoRI was inserted at the 5' end and a cleavage site for the restriction enzyme HindIII was inserted at the 3' end. The synthesized nucleic acid was cleaved with the enzymes EcoRI and HindIII and ligated with the expression vector pA27fd (described in EP-A-0382 174) which had previously been digested with EcoRI and partially digested with HindIII. The ligation preparation was transformed in *E. coli* together with the helper plasmid pUBS520 (Brinkmann et al., Gene 85 (1989), 109–114).

The clones were selected by means of the plasmid-mediated ampicillin and kanamycin resistance. The plasmid pNGF23fd that was obtained contains a smaller EcoRI/HindIII fragment than the starting plasmid pA27fd with a size of about 400 bp.

b) Expression in *E. coli*

In order to examine the expression output the *E. coli* strain transformed with the plasmids pNGF23fd and pUBS520 was cultured in LB medium (Sambrook et al., 1989, Molecular Cloning, Cold Spring Harbor) in the presence of ampicillin and kanamycin (each at 50 μg/ml final concentration) up to an OD of 550 nm. The expression was initiated by addition of 5 mM IPTG. The culture was incubated for a further 4 hours. Subsequently the *E. coli* were collected by centrifugation and resuspended in buffer (50 mM Tris-HCl pH 8, 50 mM EDTA); the *E. coli* were lysed by sonication. The insoluble protein fractions were collected by centrifuging again and resuspended in the aforementioned buffer by sonication. One quarter volume application buffer (250 mM Tris-HCl pH 6.8, 0.01 M EDTA, 5% SDS, 5% mercaptoethanol, 50% glycerol and 0.005% bromophenol blue) was added to the suspension and was analysed with the aid of a 12.5% SDS polyacrylamide gel. The same preparation using a culture of *E. coli* (pNGF23fd, pUBS520) to which IPTG had not been added was carried out as a control and applied to the polyacrylamide gel. In the preparation of the IPTG-induced culture a clear band with a molecular weight (compared to a standard protein mixture of Biorad "H+L") of about 14 kD is seen after staining the gel with 0.2% Coomassie blue R250 (dissolved in 30% methanol and 10% acetic acid). This band is not found in the preparation of the non-induced *E. coli* cells.

EXAMPLE 2

Preparation of Inclusion Bodies (=IBs)

In order to prepare the IBs containing recombinant NGF, the *E. coli* expression strain described in example 1 was fermented for 8 hours in a 10 l fermenter. NGF expression was induced by adding IPTG in the logarithmic growth phase ca. 4 hours after the start of fermentation. 690 g biomass was harvested by means of centrifugation after 8 hours fermentation. The biomass was suspended in 3.5 l 0.1 mol/l Tris-HCl pH 7 and, after addition of 0.7 g lysozyme, 7 mg DNase and 0.4 mmol/l $MgSO_4$, it was incubated for 20 minutes at 0° C. Complete cell lysis was subsequently carried out by means of high pressure dispersion at 1000 bar. DNase was again added to the lysis solution to a final concentration of 0.1 mg/ml and $MgSO_4$ to a final concentration of 2 mmol/l and the solution was incubated for 30 minutes at 20° C. After the DNase treatment the solution was diluted with a half volume of 6% Brij 35, 1.5 mol/l NaCl, 60 mmol/l EDTA, pH 7.0 and incubated for 20 minutes in an ice bath. Insoluble components (IBs) were subsequently separated by centrifugation. The precipitate was suspended in a three-fold volume of 0.1 mol/l Tris-HCl, 20 mmol/l EDTA, pH 6.5 (TE buffer). After 30 minutes incubation at 20° C., the IBs were harvested by centrifuging again. The subsequent resuspension of the precipitate was carried out in a three-fold volume of TE buffer. After 30 minutes incubation at 20° C. the IBs were obtained in the precipitate by an additional centrifugation.

In order to determine the amount of rh-NGF in the IBs, 500 mg IBs (wet weight) was made up to 10 ml with a solution of 7.5 mol/l guanidinium-HCl (GdmHCl) and 10 mmol/l EDTA, pH 6.0 and suspended for 2 hours. The protein content of the solution was determined by means of Biuret protein determination (Boehringer Mannheim, Order No. 124281). After separation of the proteins denatured with SDS and reduced with DTE in the dissolved IBs by means of SDS capillary electrophoresis, the amount of rh-NGF relative to the total protein content was determined by comparing the peak area with that of standard NGF (e.g. Boehringer Mannheim, order No. 1457616) or by densitometric measurement of the sample lanes after separation of the proteins by means of SDS gel electrophoresis. The IBs isolated from 10 l fermentation broth contained ca. 6 g rh-NGF.

EXAMPLE 3

Solubilization and Derivatization of rh-NGF a) Preparation of the Solubilisate IBs were suspended in a solution of 7.5 mol/l GdmHCl, 0.1 mol/l Tris-HCl, 10 mmol/l EDTA and 0.1 mol/l DTT, pH 8.5 at a concentration of 20 to 200 g IBs/l and stirred for 2 hours at 20–25° C. Subsequently the solution was adjusted to pH 3 with 25% HCl and cooled to ca. 4° C. The solubilisate obtained in this manner was diafiltrated at ca. 4° C. in a crossflow filtration apparatus over an ultrafiltration membrane with an exclusion limit of 10 kDa against 6–10 volumes 7.5 mol/l GdmHCl, 10 mmol/l EDTA, pH 3 or dialysed several times against the same buffer in the dialysis tube.

b) Preparation of a Derivative from the Solubilisate (state of the art)

The DTT-free dialysed solubilisate obtained in example 3a was admixed with 20 mmol/l GSSG and adjusted to pH 7.5 by titration with a solution of 1 mol/l Tris. The mixture obtained was incubated for 2 hours at ca. 20–25° C. and then adjusted to pH 6 with 25% HCl and cooled to ca. 4° C. The derivative obtained in this manner was diafiltrated at ca. 4° C. in a crossflow filtration apparatus over an ultrafiltration membrane with an exclusion limit of 10 kDa against 6–10 volumes 7.5 mol/l GdmHCl, 10 mmol/l EDTA, pH 6 or dialysed several times against the same buffer in the dialysis tube.

c) Preparation of the Derivative Directly from the IBs (process according to the invention)

IBs were suspended in a solution of 7.5 mol/l GdmHCl, 0.1 mol/l Tris-HCl, 10–200 mmol/l GSSG, 10 mmol/l EDTA, pH 6 at a concentration of 20 to 200 g IBs/l and stirred for 3 hours at 20–25° C. Subsequently the derivative obtained in this manner was diafiltrated at ca. 4° C. in a crossflow filtration apparatus over an ultrafiltration membrane with an exclusion limit of 10 kDa against 6–10 volumes 7.5 mol/l GdmHCl, 10 mmol/l EDTA, pH 6 or dialysed several times against the same buffer in the dialysis tube.

The direct derivatization of IBs was carried out in an analogous manner at pH values of 3–10 during the derivatization and pH 6 during diafiltration, the pH value was adjusted with NaOH or HCl to 6 before the dialysis. In the case of pH values below 6 the GSSG concentration is increased to 300 mmol/l. Undissolved GSSG that may be present was removed by centrifugation before the start of the derivatization.

Detection of the completed derivatization was carried out by means of SDS gel electrophoresis and mass spectroscopy (MALDI-MS). This showed that the degree of derivatization obtained by example 3c was considerably higher than the derivatization carried out according to the prior art (example 3b) independent of the pH value during the derivatization.

The renaturation behaviour of the derivative and solubilisate was examined with fresh material and material stored at 4° C. (see example 4 for details). Whereas the derivatives prepared according to 3c exhibited an unchanged renaturation behaviour after 4 weeks independent of the pH value during production (yield ca. 100% of the initial value), the renaturation yield of the solubilisate (3a) decreases to ca. 60% and the derivative (3b) prepared according to the prior art decreased to ca. 80%. This corresponded to the MALDI-MS data i.e. as expected, the stability of the derivative depends on the degree of derivatization.

EXAMPLE 4

Renaturation of rh-NGF

In order to prepare biologically active rh-NGF from the solubilisates/derivatives prepared in example 3, the solutions containing rh-NGF in an inactive, soluble form were diluted 20- to 500-fold at ca. 4° C. in renaturation buffer composed of 1 mol/l Tris-HCl, 0.5 mol/l arginine, 1 mmol/l EDTA, 1 mmol/l GSH, pH 9.1.

In order to detect renatured rh-NGF, the mixtures were quantified after an incubation period of 24 h by means of reversed phase chromatography on a POROS R1/H column (2.1×100 mm, Perseptive Biosystems, Freiburg, Germany). 5% Acetonitrile in $H_2O$ (0.1% TFA) served as the starting buffer, the elution was carried out with a gradient of up to 80% acetonitrile in $H_2O$ (0.1% TFA) over 20 min at a flow rate of 1 ml/min. Native NGF was identified by evaluating the eluate fractions in a bioassay (see below).

The ability of rh-NGF to stimulate sensory neurones from dissociated dorsal root ganglia of chicken embryos (embryonic day 8) to produce dendrites (=DRG test=dorsal root ganglion assay, Levi-Montalcini, R., Meyer, H. and Hamburger, V. 1954, Cancer Res. 14, 49–57; Varon, S., Nomura, J., Perez-Polo, J. R. and Shooter, E. M., 1972, Meth. in Neurochemistry 3, 203–229; EP-A 0335673, p 14–15, example C) was used to determine the concentrations of renatured biologically active rh-NGF in the HPLC fractions or directly in renaturation solutions.

The HPLC fractions were tested in a dilution series at concentrations of c=100 ng/ml to c=100 pg/ml in 1:2 dilution steps in 48-well plates. In this process 300 μl medium (F14 medium; Coon, M. G and Welβ, M. G., 1969, Proc. Natl. Acad. Sci. USA 62, 852–859) and 100 μl cell suspension plus 100 μl of the dilutions stated above (=final concentrations c=20 ng/ml to c=20 pg/ml) were mixed in cell culture plates from the Falcon Co. and incubated for 48 hours at 37° C. and 3.5% $CO_2$. The number of cells that had formed dendrites was quantified as a measure of the biological activity. A solution of known concentration of 2.5 S NGF from the submaxillaris glands of the mouse (Boehringer Mannheim Co.) was used as a reference. Renaturation preparations were examined analogously after centrifugation and optionally predilution with F14 medium.

EXAMPLE 5

Cloning the Catalytic Domain of the FX Protease Gene (Plasmid: pFX-CD)

Methods

Recombinant DNA Technique

Standard methods were used to manipulate DNA as described in Sambrook, J. et al. (1989) In: Molecular cloning: A laboratory manual. Cold Spring Harbor Laboratory Press, Cold Spring Harbor, New York. The molecular biological reagents were used according to the manufacturer's instructions.

Protein Determination

The protein concentration of the protease variant fFX-EGF2-AP-CD was determined by determining the optical density (OD) at 280 nm using the molar extinction coefficients calculated on the basis of the amino acid sequence ($\epsilon$=43490 $cm^2$/mol).

Expression Vector

The vector for the expression of the blood coagulation protease variants is based on the expression vector pSAM-CORE for core-streptavidin. The preparation and description of the plasmid p-SAM-CORE is described by Kopetzki, E. et al., in WO 93/09144.

The core-streptavidin gene was replaced by the desired protease variant gene in the pSAM-CORE vector.

cloning

The FX cDNA from bp position 649 to 1362, coding for the FX protease domain from amino acid position 217 to 454 (cDNA sequence acid sequence and amino acid sequence numbering according to the publication of Kaul, R. K. et al., (Gene 41 (1986) 311–314) was amplified in a polymerase chain reaction (PCR) according to the method of Mullis, K. B. and Faloona, F. A., (Methods Enzymol. 155, (1987) 350–355) using the PCR primers N1 (SEQ ID NO:1) and N2 (SEQ ID NO:2).

EcoRI BspHI
N1: 5'-AAAAAAGAATTCTCATGATCGTGGGAGGCC-AGGAATGCAAG-3'

HindIII
N2: 5'-AAAAAAAAGCTTCATTACTTGGCCTTGGGC-AAGCCCCTGGT-3' and a commercially available human liver cDNA gene bank (vector: Lambda ZAP® II) from the Stratagene Company (La Jolla, Calif., U.S.A.) as template DNA. The PCR primers introduced a singular BspHI cleavage site and an ATG start codon at the 5' end of the coding region and a singular HindIII cleavage site at the 3' end of the coding region.

The ca. 740 bp long PCR product was digested with the restriction endonucleases BspHI and HindIII and the ca. 725 bp long BspHI/HindIII-FX fragment was ligated into the ca. 2.55 kbp long NcoI/HindIII-pSAM-CORE vector fragment after purification by agarose gel electro-phoresis. The desired plasmid pFX-CD was identified by restriction mapping and the FX cDNA sequence isolated by PCR was checked by DNA sequencing.

EXAMPLE 6

Cloning of the FX Protease Gene with an EGF2 Domain, Activation Peptide and Catalytic Domain (plasmid: pFX-EGF2-AP-CD)

The FX cDNA from bp position 322 to 1362, coding for the EGF2 domain, the activation peptide and the catalytic protease domain from amino acid position 108 to 454 was amplified by means of PCR using the PCR primers N3 (SEQ ID NO:3) and N2 (SEQ ID NO:2).

EcoRI
N3: 5'
AAAAAAGAATCCATTAAAGAGGAGAAATTAA-
AATGCGGAAGCTCTGCAGCCTGGACAAC-3'
and a commercially available human liver cDNA gene bank (vector: Lambda ZAP® II) from the Stratagene Company (La Jolla, Calif., U.S.A.) as template DNA. The PCR primers introduced an ATG start codon and a singular EcoRI cleavage site at the 5' end of the coding region and a singular HindIII cleavage site at the 3' end of the coding region.

The ca. 1.09 bp long PCR product was digested with the restriction endonucleases EcoRI and BstEII and the ca. 1.02 kbp long EcoRI/BstEII-FX fragment was ligated into the ca. 2.58 kbp long EcoRI/BstEII-pFX-CD vector fragment (example 5) after purification by agarose gel electrophoresis. The desired plasmid pFX-EGF2-AP-CD was identified by restriction mapping and the FX cDNA sequence isolated by PCR was checked by DNA sequencing.

EXAMPLE 7 a) Expression of the Protease Gene in E. coli

In order to express the protease gene an E. coli K12 strain (e.g. UT5600 Grodberg, J. and Dunn, J. J. Bacteriol. 170 (1988) 1245–1253) was transformed with the expression plasmid pFX-EGF2-AP-CD, (ampicillin resistance) described in example 6 and with the lacI$^q$ repressor plasmid pUBS520 (Kanamycin resistance, preparation and description see: Brinkmann, U. et al., Gene 85 (1989) 109–114).

The transformed UT5600/pUBS520/pFX-EGF2-AP-CD cells were cultured in a shaking culture in DYT medium (1% (w/v) yeast extract, 1% (w/v) Bacto Tryptone, Difco and 0.5% NaCl) containing 50–100 mg/l ampicillin and 50 mg/l kanamycin at 37° C. up to an optical density at 550 nm ($OD_{550}$) of 0.6–0.9 and subsequently induced with IPTG (final concentration 1–5 mmol/l). After an induction phase of 4–8 hours (h) at 37° C., the cells were harvested by centrifugation (Sorvall RC-5B centrifuge, GS3 rotor, 6000 rpm, 15 min), washed with 50 mmol/l Tris-HCl buffer pH 7.2 and stored at −20° C. until further processing. The cell yield from a 1 l shaking culture was 4–5 g (wet weight).

b) Expression Analysis

The cell pellets from in each case 1 ml centrifuged culture medium (UT5600/pUBS520/pFX-EGF2-AP-CD cells) were resuspended in 0.25 ml 10 mmol/l Tris-HCl, pH 7.2 and the cells were lysed by ultrasonic treatment (2 pulses of 30 s at 50% intensity) using a Sonifier® Cell Disruptor B15 from the Branson Company (Heusenstamm, Germany). The insoluble cell components were sedimented (Eppendorf 5415 centrifuge, 14000 rpm, 5 min) and 1/5 volumes (vol) 5 ×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction (pellet) was resuspended in 0.3 ml 1×SDS sample buffer containing 6–8 M urea, the samples were incubated for 5 min at 95° C. and centrifuged again. Afterwards the proteins were separated by SDS polyacrylamide gel electrophoresis (PAGE) (Laemmli, U. K., Nature 227 (1970) 680–685) and stained with Coomassie Brilliant Blue R dye.

The FX-EGF2-AP-CD protease variant synthesized in E. coli was homogeneous and was exclusively found in the insoluble cell debris fraction (inclusion bodies, IBs). The expression yield was ca. 50% relative to the total E. coli protein.

EXAMPLE 8

Cell Lysis, solubilization and Preparation of Inclusion Bodies (IBs)

The cell pellet from 3 l shaking culture (ca. 15 g wet weight) was resuspended in 75 ml 50 mmol/l Tris-HCl, pH 7.2. The suspension was admixed with 0.25 mg/ml lysozyme and it was incubated for 30 min at 0° C. After addition of 2 mmol/l $MgCl_2$ and 10 µg/ml DNase I (Boehringer Mannhein GmbH, catalogue No. 104159) the cells were disrupted mechanically by means of high pressure dispersion in a French® Press from the SLM Amico Company (Urbana, IL, USA). Subsequently the DNA was digested for 30 min at room temperature (RT). 37.5 ml 50 mmol/l Tris-HCl pH 7.2, 60 mmol/l EDTA, 1.5 mol/l NaCl, 6% Brij X-100 was added to the preparation, it was incubated for a further 30 min at RT and centrifuged in a Sorvall RC-5B centrifuge (GSA Rotor, 12000 rpm, 15 min). The supernatant was discarded, 100 ml 50 mmol/l Tris-HCl, pH 7.2, 20 mmol/l EDTA was added to the pellet, it was incubated for 30 min at 4° C. while stirring and again sedimented. The last wash step was repeated. The purified IBs (1.5–2.0 g wet weight, 25–30% dry mass, 100–150 mg protease) were stored at −20° C. until further processing.

EXAMPLE 9

Solubilization and Reduction/derivatization and Dialysis of the IBs

The purified IBs were suspended at a concentration of 100 mg IB pellet (wet weight)/ml corresponding to 5–10 mg/ml protein in 6 mol/l guanidinium-HCl, 100 mmol/l Tris-HCl, 20 mmol/l EDTA, pH 8.0 and aliquots were dissolved while stirring in the presence of 200 mmol/l GSSG or 200 mmol/l GSH within 1 to 3 hours at room temperature. Afterwards the pH was adjusted to pH 5.0 and the insoluble components were separated by centrifugation (Sorvall RC-5B centrifuge, SS34 rotor, 16000 rpm, 15 min) and dialysed for 24 hours at 4° C. against 6 mol/l guanidinium-HCl pH 5.0. The derivatization was detected by means of SDS-PAGE.

EXAMPLE 10

Dependence of the Renaturation of FX-EGF2-AP-CD on the Reduction/Derivatization

The FX-EGF2-AP-CD protease variant solubilized in 6 mol/l guanidinium HCl and reduced with 100 mmol/l DTE or derivatized with different concentrations of GSSG/GSH was renatured at 4° C. by a single addition of 50 µl IB solubilisate/derivative in each case to 5 ml renaturation buffer (50 mmol/l Tris-HCl, 0.6 mol/l arginine/10 mmol/l $CaCl_2$/2 mmol/l EDTA/ 2 mmol/l GSH/0.5 mmol/l GSSG, pH 8.5).

The renatured protein was dialysed twice against 100 vol. 50 mmol/l Tris-HCl, 150 mmol/l NaCl, 5 mmol/l $CaCl_2$, 0.1% polyethylene glycol 8000 (PEG 8000), pH 8.0 for 8–16 h at 4° C. The precipitated protein was separated by centrifugation (Eppendorf 5415 centrifuge, 14000 rpm, 5 min) and the clear supernatant was used for the activation.

EXAMPLE 11

Activation of the rFX-EGF2-AP-CD Protease Variant with RVV-X

In each case 1 ml of the renatured and dialysed rFIX-EGF2-AP-CD samples was admixed with 10 μl of Russel's viper venom (RVV) solution (1 mg/ml lyophilisate dissolved in 20 mmol/l Tris-HCl, pH 7.6) from the Sigma Aldrich Chemie GmbH Co. (Deisenhofen, GFR) and incubated at 37° C. for 1–2 days. The time course of the enzymatic rFX-EGF2-AP-CD activation was monitored using the chromogenic peptide substrate Chromozym X (see example 12) until completion of the digestion (plateau, maximum activation). For this samples (20 μl) were taken from the reaction mixture at intervals of 4–6 h and the generated FXa activity was determined.

EXAMPLE 12

FXa Activity Test

The activity of renatured and activated rFXa-EGF2-AP-CD was determined using the chromogenic substrate Chromozym X from Boehringer Mannheim GmbH (Mannheim, GFR, cat.No. 789763). 20 μl sample was admixed with 180 μl 50 mmol/l Tris-HCl, 150 mmol/l NaCl, 5 mml/l $CaCl_2$, 0.1% PEG 8000, pH 8.0 and 20 μl 4 mmol/l Chromozym X in a microtitre plate at RT and the linear initial slope (ΔA/min) was determined by absorbance measurements at a wavelength of 405 nm in an ELISA reader.

Test principle:

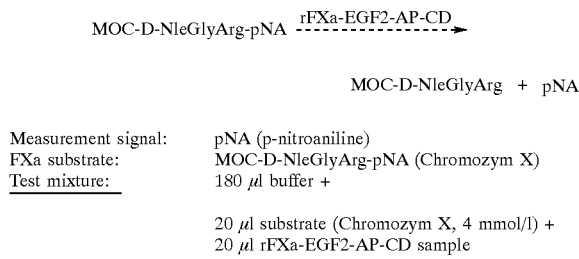

MOC-D-NleGlyArg + pNA

| Measurement signal: | pNA (p-nitroaniline) |
| FXa substrate: | MOC-D-NleGlyArg-pNA (Chromozym X) |
| Test mixture: | 180 μl buffer + |
| | 20 μl substrate (Chromozym X, 4 mmol/l) + |
| | 20 μl rFXa-EGF2-AP-CD sample |

EXAMPLE 13

Determination of the Renaturation Efficiency

The generated rFXa-EGF2-AP-CD activity (plateau value) was used to calculate the renaturation efficiency. The highest value within the measurement series serves as a reference which was set to 100%.

The reduced protein results in a renaturation yield of ca. 60% compared to derivatized protein.

List of References

Bailey, J. L., Cole, R. D., J. Biol. Chem. 234 (1959) 1733–1739

Beattie and Fowle, Nature 352 (1991) 548–549

Biochem. Biophys. Res. Commun. 171 (1990) 116–122

Brinkmann et al., Gene 85 (1989) 109–114

Cole, R. D., Meth. Enzymol. 11 (1967) 206–208

Coon, M. G. and Weiβ, M. G., Proc. Natl. Acad. Sci. USA 62 (1969) 852–859

EP-A 0 093 619

EP-A 0 114 506

EP-A 0 114 507

EP-A 0 241 022

EP-A 0 253 823

EP-A 0 329 175

EP-A 0 335 673

EP-A 0 361 475

EP-A 0 364 926

EP-A 0 370 171

EP-A 0 382 174

EP-A 0 414 151

EP-A 0 450 386

EP-B 0 121 338 (U.S. Pat. No. 5,169,762)

Gene 70 (1988) 57–65

Grodberg, J.; Dunn, J. J.: J. Bacteriol. 170 (1988) 1245–1253

Heath, W. F. et al., J. Biol. Chem. 267 (1992) 419–425

Kaul, R. K., Hildebrand, B.; Roberts, S.; Jagadeeswaran, P., Gene 41 (1986) 311–314

Laemmli, U. K., Nature 227 (1970) 680–685

Leibrock et al.,.Nature 341 (1989) 149–152 Levi-Montalcini, R., Meyer, H. and Hamburger, V., Cancer Res. 14 (1954) 49–57

Marston F. A. O., Biochem. J. 214 (1986) 1–12

Mullis, K. B.; Faloona, F. A., Methods Enzymol. 155 (1987) 350–355

Sambrook, J.; Fritsch, E. F.; Maniatis, T.: Molecular Cloning: A Laboratory manual. Cold Spring Harbor Press, Cold Spring Harbor, N.Y., (1989)

Thannhauser, T. W., Konishi, Y., Sheraga, H. A., Analyt. Biochem 138 (1984) 181–188

Thannhauser, T. W., Scheraga, H. A., Biochemistry 24 (1985) 7681–7688

Ullrich et al., Nature 303 (1983) 821–825

U.S. Pat. 4,933,434

Varon, S., Nomura, J., Perez-Polo, J. R. and Shooter, E. M., Meth. in Neurochemistry 3 (1972) 203–229

Wetzel, R. et al., Gene 16 (1981) 63–71

WO 87/02673

WO 91/03568

WO 91/08762

WO 92/22665

WO 93/09144

WO 93/19084

WO 95/30686

What is claimed is:

1. A process for forming a mixed disulfide of a recombinant protein present in an inclusion body, comprising:
   (a) in a first step, solubilizing said inclusion body with a denaturing agent in the presence of a disulphide component to provide solubilized recombinant protein, followed by;
   (b) derivatizing said solubilized recombinant protein in a second step by adding disulphide component in the presence of said denaturing agent at a concentration sufficient to form a mixed disulfide.

2. The process of claim 1, wherein said denaturing agent is guanidinium hydrochloride or urea.

3. The process of claim 1, wherein said disulfide component is selected from the group consisting of GSSG, cystamine and cystine.

4. The process of claim 1, wherein said disulfide component is used at a concentration of at least 1 mmol/l.

5. The process of claim 1, wherein said disulfide component is at a concentration of from 1 to 1000 mmole/l.

6. The process of claim 3, wherein said disulfide component is GSSG or cystamine at a concentration of at least 10 mmole/l.

7. The process of claim 1, wherein said recombinant protein and disulfide component are at a molar ratio ranging from 1:1 to 1:10000.

8. The process of claim 7, wherein said recombinant protein and disulfide component are at a molar concentration ratio of 1:1000.

9. The process of claim 1, wherein said recombinant protein is a neurotrophin.

10. The process of claim 9, comprising derivatizing said neurotrophin at a pH less than 7.

11. The process of claim 10, wherein the pH is from 3 to 6.5.

12. The process of claim 1, further comprising adding a reducing agent.

13. The process of claim 1, comprising solubilizing said inclusion body with an amount of EDTA sufficient to protect any free SH groups on said recombinant protein.

14. The process of claim 13, wherein said EDTA is at a concentration of from 0.1 to 100 mmole/l.

15. The process of claim 1, further comprising separating said mixed disulfides from any unreacted disulfide component.

16. The process of claim 15, comprising separating said mixed disulfides and disulfide component via dialysis.

17. The process of claim 16, comprising dialyzing with a solution containing a denaturing agent.

18. The process of claim 16, comprising dialyzing with a solution containing 1 mmol/l HCl.

19. A process for activating a recombinant protein of an inclusion body, comprising:
   (i) solubilizing a recombinant protein containing inclusion body in a solution which contains a denaturing concentration of a denaturing agent and a disulfide component
   to form a mixed disulfide between said recombinant protein and said disulfide component and subsequently removing said disulfide component; and
   (ii) adding a reducing agent in an amount sufficient to activate said recombinant protein.

20. The process of claim 19, wherein the reducing agent is a mercaptan.

21. The process of claim 20, wherein said mercaptan is reduced glutathione (GSH), 2-mercaptoethanol, dithioerythritol (DTE), or diethiothreitol (DTT).

22. The process of claim 19, wherein said reducing agent is a salt of sulfurous acid.

23. The process of claim 19, wherein said reducing agent is at a concentration of from 0.01 to 50 mmole/l.

24. The process of claim 19, comprising activating said recombinant protein from 0.1 to 100 hours.

25. The process of claim 19, comprising activating said recombinant protein in the presence of EDTA.

26. The process of claim 19, comprising activating said recombinant protein in the presence of a radical interceptor.

27. The process of claim 19, comprising activating said recombinant protein in the presence of GSH and GSSG.

28. The process of claim 27, wherein said GSH is at a concentration of from 0.1 to 20 mmol/l, and said GSSG is at a concentration of from 0.01 to 10 mmol/l.

29. The process of claim 14, comprising activating said recombinant protein over a period of 1–300 hours.

30. The process of claim 14, wherein said recombinant protein is a protease, a growth factor, a protein hormone, or a cytokine.

31. The process of claim 20, wherein said recombinant protein hormone is a neurotrophin.

32. The process of claim 1, comprising derivatizing said protein at a pH less than 7.0.

33. The process of claim 32, wherein said pH is from 3 to 6.5.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 1:

AAAAAAGAAT TCTCATGATC GTGGGAGGCC AGGAATGCAA G                          41

(2) INFORMATION FOR SEQ ID NO: 2:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 2:

AAAAAAAAGC TTCATTACTT GGCCTTGGGC AAGCCCCTGG T                          41

(2) INFORMATION FOR SEQ ID NO: 3:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 3:

AAAAAAGAAT CCATTAAAGA GGAGAAATTA AAATGCGGAA GCTCTGCAGC CTGGACAAC       59

(2) INFORMATION FOR SEQ ID NO: 4:

(i) SEQUENCE CHARACTERISTICS:
        (A) LENGTH: 394 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

AGAATTCAAG AAGGAGATAT ACATATGTCA TCATCACATC CAATCTTCCA CAGGGGCGAG      60

TTCTCGGTGT GTGACAGTGT CAGCGTGTGG GTTGGGGATA AGACCACCGC CACAGATATC    120

AAGGGCAAGG AGGTGATGGT GTTGGGAGAG GTGAACATTA ACAACAGTGT ATTCAAACAG    180

TACTTTTTTG AGACCAAGTG CCGGGACCCA AATCCCGTCG ACAGCGGGTG CCGGGGCATT    240

GACTCAAAGC ACTGGAACTC ATATTGTACC ACGACTCACA CCTTTGTCAA GGCGCTGACC    300

-continued

```
ATGGATGGCA AGCAGGCTGC CTGGCGGTTT ATCCGGATAG ATACGGCCTG TGTGTGTGTG        360

CTCTCTAGAA AGGCTGTGAG ATGATAAAAG CTTG                                   394
```